United States Patent
Baudino

[11] Patent Number: 6,044,304
[45] Date of Patent: Mar. 28, 2000

[54] BURR RING WITH INTEGRAL LEAD/CATHETER FIXATION DEVICE

[75] Inventor: Michael D. Baudino, Coon Rapids, Minn.

[73] Assignee: Medtronic, Inc., Minneapolis, Minn.

[21] Appl. No.: 09/067,974

[22] Filed: Apr. 29, 1998

[51] Int. Cl.[7] .................................................. A61N 1/02
[52] U.S. Cl. .......................... 607/116; 600/378; 604/175
[58] Field of Search .................... 600/377, 378, 600/561; 604/175; 606/129, 130; 607/116, 139

[56] References Cited

U.S. PATENT DOCUMENTS

| | | | |
|---|---|---|---|
| 3,402,710 | 9/1968 | Paleschuck | 604/175 |
| 3,444,861 | 5/1969 | Schulte | 604/175 |
| 4,328,813 | 5/1982 | Ray | 128/791 |
| 4,350,159 | 9/1982 | Gouda | 128/303 |
| 4,662,600 | 5/1987 | Watson | 604/8 |
| 4,826,487 | 5/1989 | Winter | 604/175 |
| 5,057,084 | 10/1991 | Ensminger et al. | 604/175 |
| 5,464,446 | 11/1995 | Dreessen | 607/116 |
| 5,843,150 | 12/1998 | Dreessen et al. | 607/116 |

FOREIGN PATENT DOCUMENTS 9633766  10/1996  WIPO .

*Primary Examiner*—Lee Cohen
*Attorney, Agent, or Firm*—Banner & Witcoff, Ltd.

[57] ABSTRACT

The present invention is a method and apparatus for securing an implantable lead within a brain of a patient comprising a bur ring and a septum contained within an aperture of the bur ring. The burr ring may be secured to a skull portion of the brain and the septum accepts and secures the lead in a substantially fixed position relative to the brain. The septum may be composed of a silicone rubber, elastomer, polyurethane, or butyl rubber. The septum may have a sold composition, a porous composition, or one have at least one blind hole for accepting the lead. The burr ring may include a one or more guides positioned along an upper flange portion of the burr ring accepting the lead and a cap capable of being positioned to close the aperture of the burr ring.

24 Claims, 4 Drawing Sheets

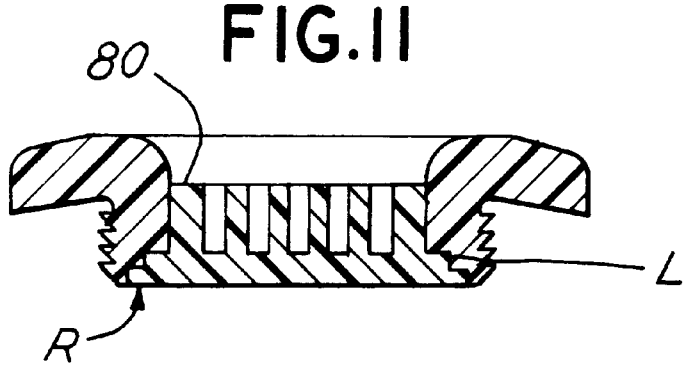
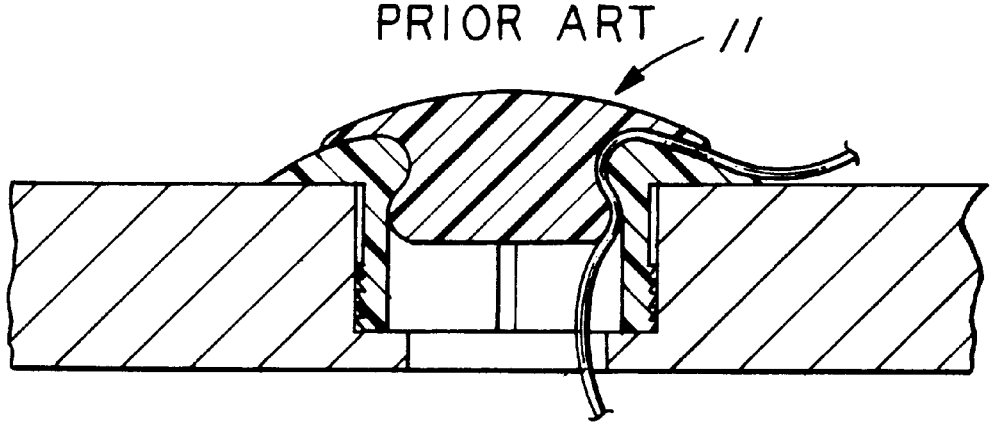

BURR RING WITH INTEGRAL LEAD/CATHETER FIXATION DEVICE

BACKGROUND OF THE INVENTION

1. Field of the Invention

The present invention relates generally to methods and apparatus for securing medical devices and more particularly methods and apparatus for securing medical devices such as parenchymal catheters or electrical stimulation leads within a cranial burr hole.

2. Description of the Related Art

Medical procedures involving access to the brain through a burr hole in the skull are under increasing use. Two such procedures are electrical stimulation of the brain for such purposes as relief of chronic pain and treatment of movement disorders, and the use of parenchymal catheters for infusing pharmaceutical agents. A typical electrical brain stimulation system comprises a pulse generator operatively connected to the brain by a lead having at its distal end an electrode designed to be implanted within the brain, and having at its proximal end a connector assembly designed to connect to the pulse generator. Use of a parenchymal catheter generally involves the insertion of a catheter within the brain to dispense pharmaceutical agents at a specific desired location.

One critical aspect of the above-listed procedures, and of any other such procedures that involve instrument access to the brain through a burr hole, is the precision with which any such inserted devices, e.g. catheters and leads, are placed. Once a satisfactory burr hole is established at a particular site, to avoid unintended injury to the brain, physicians typically use stereotactic procedures to position the inserted devices. One stereotactic instrument which may be used, for example, to position a lead electrode is disclosed in U.S. Pat. No. 4,350,159 to Gouda, incorporated herein by reference. As can be appreciated, once an inserted device is properly positioned, it is important that the device not be moved. Even one millimeter of travel of the positioned device may cause unsatisfactory results or, in some cases, severe injury to the brain. Accordingly, reliable methods and apparatus for fixing the positioned device at the burr hole are necessary.

Previous designs of systems for securing a positioned device within a burr hole have a number of drawbacks. U.S. Pat. No. 4,328,813 to Ray, incorporated herein by reference, discloses a socket and cap arrangement in which the cap is positioned so as to trap a positioned electrical stimulation lead between the socket and cap by friction. That arrangement involves securing the lead off center from the burr hole in a manner such that during installation of the anchoring cap the lead is secured in place. The lead, however, often needs to be manually supported in place while the anchoring cap is being installed. The lead is thus susceptible to inadvertent movement by the physician during the cap installation period. Further, in the interaction of the cap and socket, the lip of the cap tends to pull on the lead and to cause its dislodgement.

Previous systems also are susceptible to leakage of cerebrospinal fluid (CSF) during the operating procedure to implant the burr ring and lead or catheter. The present invention is directed to overcoming the disadvantages of the foregoing systems.

SUMMARY OF THE INVENTION

As explained in more detail below, the present invention overcomes the above-noted and other shortcomings of prior burr hole anchoring devices and methods.

The present invention preferably comprises an apparatus and method of fixing a lead or catheter at a cranial burr hole. The invention has the advantages that it allows anchoring to occur before the lead or catheter is detached from the stereotactic apparatus, thereby reducing the possibility of movement. Moreover, the lead or catheter can be fixed at any point that it may pass through the burr hole while still keeping access to the surface of the brain open.

Three separate embodiments of the present invention are described herein, each generally using a septum positioned within the circle formed by the burr hole cap. The lead or catheter is inserted through the septum which also retains the lead or catheter in a substantially fixed position relative to burr ring and the human brain. The various embodiments of the present invention differ by the type of septum being used. The septum of the present invention may have a solid composition, a porous composition or have one having at least one blind, pre-molded hole. The septum is preferably a silicone rubber material or can be a similar elastomeric material. A lead or catheter may be inserted into the brain through the septum. The septum accepts the lead or catheter and holds the lead or catheter in a fixed position relative to the burr ring and the brain. The lead or catheter may thereby be positioned and maintained in a fixed position to allow electrical stimulation or drug infusion with improved precision and accuracy.

The burr ring preferably has one or more guides to accept the lead or catheter once it has been inserted in the brain and direct it out radially from the center of the burr ring. A cap may then be placed over the septum area.

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 10 is a cross-sectional view of the burr hole ring assembly shown in FIG. 1 in accordance with another embodiment of the present invention; and FIG. 11 is a cross-sectional view of the burr hole ring assembly shown in FIG. 7 in accordance with another embodiment of the present invention.

FIG. 12 is a cross-sectional view of a burr hole ring assembly of the prior art having a cap 11.

DESCRIPTION OF THE PREFERRED EMBODIMENTS

Figure 1:
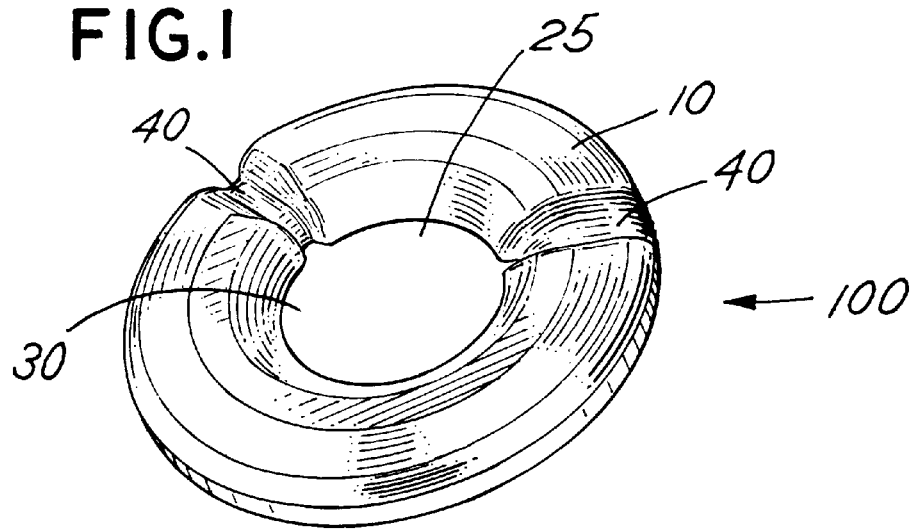
FIG. 1 is an illustration of an exemplary burr hole ring assembly in accordance with the present invention.
Figure 2:
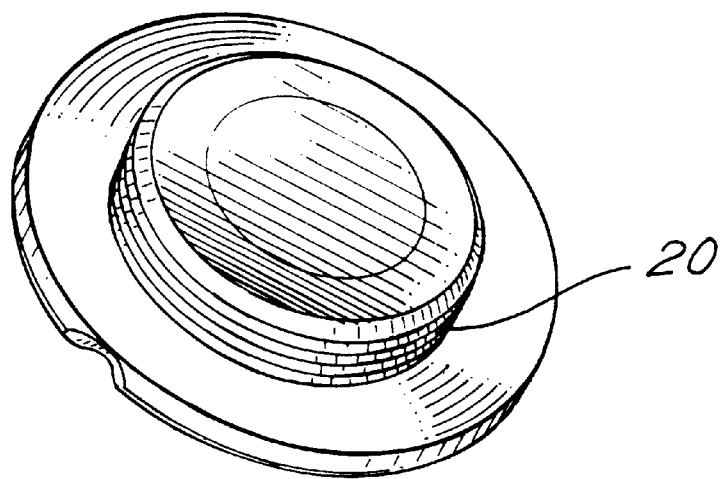
FIG. 2 is another view of the burr hole ring assembly shown in FIG. 1.

Referring to FIGS. 1 and 2, a preferred form of the burr ring 100 of the present invention, the burr ring 100 generally has an upper flange portion 10, circumferential ribs 20, an aperture 25, a septum 30, and one or more guides 40. The circumferential ribs 20 are positioned below the flange portion 10 and run along the periphery of the outer wall surface of the burr ring 100 as indicated. The ribs 20 engage with the side wall of a burr hole to enhance the security of the mechanical engagement of the burr ring 100 with the burr hole in the skull, or engage another ring previously placed at the burr hole, and assist in preventing dislodgement of the burr ring 100. The septum 30 is positioned within the aperture of the burr ring 100 thereby closing off the opening of the aperture. A lead is inserted into cranial cavity through the septum 30 which is a penetrable material. Guides 40 are placed in one or more places of the flange portion 10 and provide a path for positioning of the lead or catheter. Once a lead is inserted through the septum 30 of the burr ring 100, the portion of the lead protruding from the burr ring 100 may be bent to the side and placed over guide 40 to direct the lead radially outward in the direction of the guide 40. Once the lead is placed and positioned in the guide 40, a flexible cap (not shown) may be installed to engage the burr ring 100 to close off the aperture 25 along the upper flange portion, mechanically isolate the aperture 25 and stabilize the inserted lead. Typically, the cap is a silicone elastomer member configured to engage the burr ring 100. The septum 30 serves to maintain the lead in a substantially fixed position relative to the burr ring and to prevent leakage of CSF. Other embodiments of the septum 30 are described in further detail herein.

Figure 3:
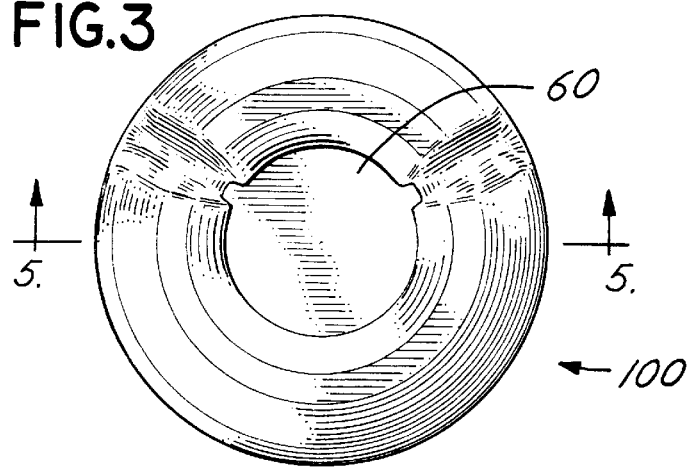
FIG. 3 is a top plan view of the burr hole ring assembly shown in FIG. 1.
Figure 4:
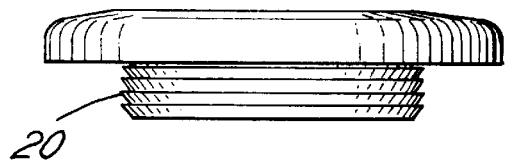
FIG. 4 is a side view of the burr hole ring assembly shown in FIG. 1.
Figure 5:
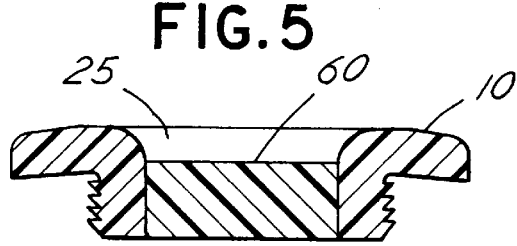
FIG. 5 is a cross-sectional view of the burr hole ring assembly shown in FIG. 1 in accordance with one embodiment of the present invention.

FIGS. 3, 4 and 5 respectively show a top plan view, side view and cross-sectional side view of the burr ring 100 of FIGS. 1 and 2. The burr ring 100 is preferably about 0.8 inches at its maximum outside diameter, 0.5 inches at its outside diameter along the circumferential ribs 20, and 0.25–0.3 inches at its inside diameter. The septum 60 is preferably in the range of 0.25 inches in thickness. Those skilled in the art will appreciate that the invention may incorporate a variety of other dimensions.

Figure 6:
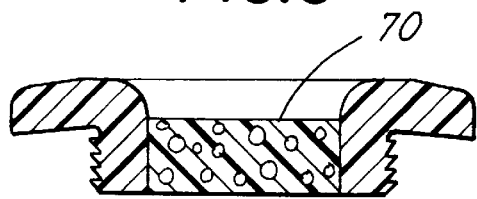
FIG. 6 is a cross-sectional view of the burr hole ring assembly shown in FIG. 1 having a porous septum in accordance with another embodiment of the present invention.

Septum 60 is a preferably made of a solid elastomeric material. In one embodiment, septum 60 is made of silicone rubber having a durometer range of 25 Shore A to 65 Shore A, and preferably 50 Shore A. Other elastomeric materials may alternatively be used including, but not limited to, biocompatible elastomer, polyurethane, butyl rubbers and the like. The septum 60 may be placed in connection with the burr ring 100 by a number of mechanisms including, for example, mechanical interlock such as grooves, adhesive, interference fit, or combinations of such. As preferred, a mechanical interlock with an adhesive seal is used as shown in FIGS. 10 and 11 (discussed herein). For example, FIG. 10 shows two circular lips L on the septum 60 to fix it within the burr ring 100. FIG. 6 shows another embodiment of the burr ring 100 using a porous elastomeric septum 70. The porous septum 70 may be made from the same materials as septum 60. Porous septum 70 may be made porous by a variety of techniques such as, for example, encapsulation of gas bubbles during vulcanization, leachable filter materials, or multiple part assembly of noncommunicating layered honeycombed structures. Porosity levels of porous septum 70 may be up to 50% with pore sizes ranging from 0.010 to 0.020 inches.

Figure 7:
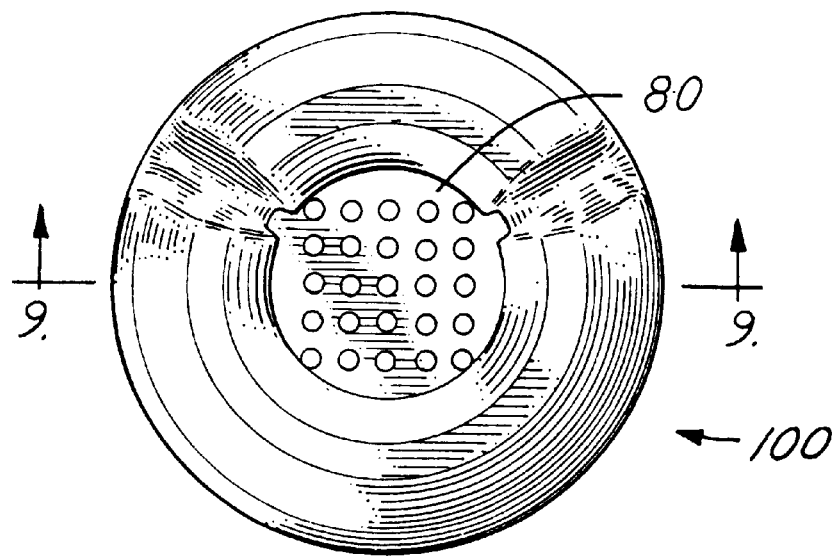
FIG. 7 is a top plan view of the burr hole ring having a blind hole septum in accordance with another embodiment of the present invention.
Figure 8:
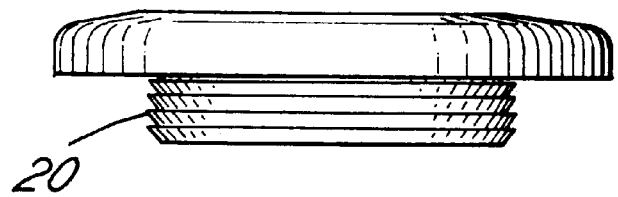
FIG. 8 is a side view of the burr hole ring assembly shown in FIG. 7.
Figure 9:
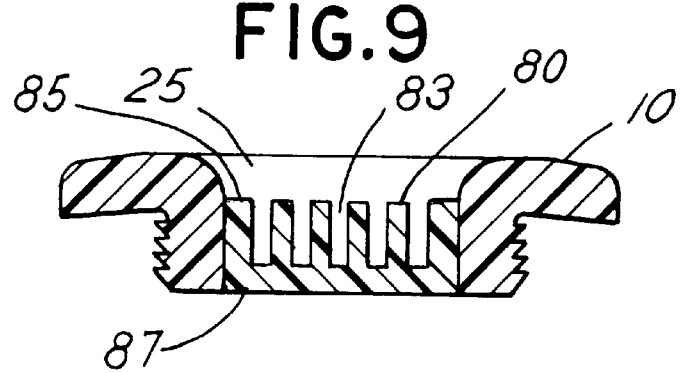
FIG. 9 is a cross-sectional view of the burr hole ring assembly shown in FIG. 7.

FIGS. 7, 8 and 9 respectively show a top plan view, side view and cross-sectional side view of another embodiment of the burr ring 100 having a blind hole septum. The blind hole septum 80 in this embodiment has a number of blind, pre-molded cavities 83 equally spaced throughout the top portion 85 of the septum 80. The cavities 83 preferably located as shown on FIG. 6 are configured to receive the lead. The lower portion 87 of the blind hole septum 80 in the cavity 83 may be punctured by the lead as it enters the cranial cavity. The blind hole septum 80 may be of any elastomeric material described above. The size of the blind holes are proportional to the device that would be inserted into the brain. For example, in the case where a brain lead is used having a 0.050 inch outside diameter, the blind holes are preferably 10% smaller in diameter to provide an interference fit between the brain lead and the blind hole cavity in septum 80. The interference fit thereby prevents CSF leakage. The number of blind holes is dependent upon the size of the burr ring 100, particularly the inside diameter. Preferably, the holes are sufficiently spaced apart to provide adequate support for the interference fit and sealing of the septum 80 with the burr ring 100. In addition, the holes are preferably sized such that removal of the lead will reseal the septum to prevent the CSF leakage. As preferred, blind holes account for approximately 50% of the exposed surface area of the blind hole septum 80. The thickness of the lower portion 87 of the septum 80 below the blind hole is in the range of 0.060 to 0.100 inches. FIG. 11 shows a circular lip and a retainer ring R that compresses and captures the septum 80 relative to the burr ring 100.

As used herein, the term "lead" refers to any elongated medical apparatus having proximal and distal ends, the distal end being extendable through a burr hole. The lead is to be anchored relative to a known location within the burr hole, so that the location of the distal end of the apparatus at, near, or within the area to be treated may be controlled. The term lead may refer to an electrode providing electrical stimulation or a parenchymal catheter for infusing pharmaceutical agents. Where a positioned device is either an electrical stimulation lead or catheter extending through a cranial burr hole, the distal end of the positioned device typically will be situated within the brain, and the desired control of that end will be holding the distal end as stationary as possible.

Retention assemblies in accordance with the present invention can be placed directly within a burr hole or within a pre-positioned burr ring. Whether a separate burr ring is used with a particular patient will depend on the specific circumstances involved in that patient's case. Further, as one might imagine, there are many possible sizes and shapes of burr rings. The selection of one burr ring over another will depend on numerous factors such as the size or shape of the burr hole, whether there is a need to hold multiple snap rings, etc. Thus, it should be understood that the following description, by way of example, shows exemplary burr ring configurations which may be used in connection with the present invention. Additionally, as noted previously herein, the device retaining mechanism may be formed as an integral portion of the burr ring, or it may be formed as a part of a separate member selectively attachable to the burr hole ring. Such a separate burr hole ring would typically be pre-placed within the burr hole, with the retention mechanism carrying member insertable into the pre-placed burr hole ring. The exemplary configurations of retaining mechanisms disclosed herein are depicted as septums which would be independently engageable with a burr ring assembly. It should be already understood, however, that each of the disclosed retaining mechanisms may be integrally formed with the burr ring.

Although the preferred embodiments of this invention have been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

I claim:

1. A device for securing an implantable lead within a brain of a patient comprising:
   (a) a burr ring capable of being secured to a skull portion of the brain and having an aperture; and
   (b) a septum contained within the aperture of the burr ring capable of accepting the lead at a plurality of locations along a surface of the septum and of securing the lead in a substantially fixed position relative to the brain.

2. A device of claim 1, wherein the septum is composed of a material selected from the group consisting of silicone rubber, elastomer, polyurethane, and butyl rubber.

3. A device of claim 1, wherein the septum is a porous material.

4. A device of claim 1, wherein the septum includes at least one blind hole for accepting and holding the lead.

5. A device of claim 1, further comprising at least one guide positioned along an upper flange portion of the burr ring for accepting the lead.

6. A device of claim 1, wherein the lead is an electrode.

7. A device of claim 1, wherein the lead is a catheter.

8. A device of claim 1, further comprising a cap capable of being positioned to close the aperture of the burr ring along an upper flange portion of the burr ring.

9. A method of securing an implantable lead having a distal end and a proximal end such that the distal end is positioned near a predetermined portion of a brain of a patient comprising the steps of:
   (a) securing a burr ring to a skull portion of the patient, the burr ring having an aperture and a septum contained within the aperture;
   (b) inserting the lead into the septum from amongst a plurality of locations along a surface of the septum in the direction of the predetermined portion of the brain; and
   (c) forwarding the lead into the brain through the septum until the distal end of the lead is positioned near the predetermined portion of the brain.

10. A method of claim 9, wherein the burr ring also has at least one guide along an upper flange portion, and further comprising the step of bending a portion of the lead near the septum and positioning the lead over one guide to direct the lead in an outward direction from the burr ring.

11. A method of claim 9, further comprising the step placing a cap to cover the aperture along an upper flange portion of the burr ring.

12. A method of claim 9, wherein the step of inserting includes the step of inserting the lead into a blind hole of the septum.

13. A device for securing an implantable lead within a brain of a patient comprising:
   (a) a burr ring capable of being secured to a skull portion of the brain and having an aperture; and
   (b) a septum contained within the aperture of the burr ring capable of accepting and securing the lead in a substantially fixed position relative to the brain and of projecting the lead along one of a possible plurality of trajectories into the brain.

14. A device of claim 13, wherein the septum is composed of a material selected from the group consisting of silicone rubber, elastomer, polyurethane, and butyl rubber.

15. A device of claim 13, wherein the septum is a porous material.

16. A device of claim 13, wherein the septum includes at least one blind hole for accepting and holding the lead.

17. A device of claim 13, further comprising at least one guide positioned along an upper flange portion of the burr ring for accepting the lead.

18. A device of claim 13, wherein the lead is an electrode.

19. A device of claim 13, wherein the lead is a catheter.

20. A device of claim 13, further comprising a cap capable of being positioned to close the aperture of the burr ring along an upper flange portion of the burr ring.

21. A method of securing an implantable lead having a distal end and a proximal end such that the distal end is positioned near a predetermined portion of a brain of a patient comprising the steps of:
   (a) securing a burr ring to a skull portion of the patient, the burr ring having an aperture and a septum contained within the aperture;
   (b) inserting the lead into the septum in the direction of the predetermined portion of the brain, the septum capable of directing the lead along one of a possible plurality of trajectories into the brain; and
   (c) forwarding the lead into the brain through the septum until the distal end of the lead is positioned near the predetermined portion of the brain.

22. A method of claim 21, wherein the burr ring also has at least one guide along an upper flange portion, and further comprising the step of bending a portion of the lead near the septum and positioning the lead over one guide to direct the lead in an outward direction from the burr ring.

23. A method of claim 21, further comprising the step placing a cap to cover the aperture along an upper flange portion of the burr ring.

24. A method of claim 21, wherein the step of inserting includes the step of inserting the lead into a blind hole of the septum.

* * * * *